(12) United States Patent
Arima et al.

(10) Patent No.: US 9,028,886 B2
(45) Date of Patent: May 12, 2015

(54) DEGRADATION INHIBITOR FOR FLAVOR OR AROMA

(75) Inventors: Tsuyoshi Arima, Urayasu (JP); Hideki Masuda, Urayasu (JP)

(73) Assignee: Ogawa & Co., Ltd., Tokyo (JP)

( * ) Notice: Subject to any disclaimer, the term of this patent is extended or adjusted under 35 U.S.C. 154(b) by 615 days.

(21) Appl. No.: 12/668,943

(22) PCT Filed: Jul. 10, 2008

(86) PCT No.: PCT/JP2008/062449
§ 371 (c)(1),
(2), (4) Date: Jan. 13, 2010

(87) PCT Pub. No.: WO2009/011271
PCT Pub. Date: Jan. 22, 2009

(65) Prior Publication Data
US 2010/0189822 A1    Jul. 29, 2010

(30) Foreign Application Priority Data
Jul. 13, 2007 (JP) ................................. 2007-183923

(51) Int. Cl.
*A61K 36/00* (2006.01)
*A61K 36/752* (2006.01)
*A61K 36/82* (2006.01)
*A23L 1/221* (2006.01)
*A23F 3/16* (2006.01)
*A23L 1/22* (2006.01)
*A23L 1/226* (2006.01)
*A23L 1/24* (2006.01)
*A23L 2/44* (2006.01)
*A23L 2/56* (2006.01)
*A23L 3/3463* (2006.01)
*A23L 3/3472* (2006.01)
*A23L 3/3571* (2006.01)
*A61K 8/66* (2006.01)
*A61K 8/92* (2006.01)
*A61K 8/97* (2006.01)
*A61Q 19/00* (2006.01)
*C11B 5/00* (2006.01)
*C11B 9/00* (2006.01)
*A61Q 11/00* (2006.01)
*A61Q 13/00* (2006.01)

(52) U.S. Cl.
CPC ............... *A23L 1/221* (2013.01); *A23F 3/166* (2013.01); *A23L 1/22008* (2013.01); *A23L 1/22635* (2013.01); *A23L 1/22642* (2013.01); *A23L 1/22657* (2013.01); *A23L 1/24* (2013.01); *A23L 2/44* (2013.01); *A23L 2/56* (2013.01); *A23L 3/3463* (2013.01); *A23L 3/3472* (2013.01); *A23L 3/3571* (2013.01); *A23V 2002/00* (2013.01); *A61K 8/66* (2013.01); *A61K 8/922* (2013.01); *A61K 8/97* (2013.01); *A61K 2800/52* (2013.01); *A61K 2800/524* (2013.01); *A61K 2800/85* (2013.01); *A61Q 11/00* (2013.01); *A61Q 13/00* (2013.01); *A61Q 19/00* (2013.01); *C11B 5/00* (2013.01); *C11B 5/0078* (2013.01); *C11B 5/0085* (2013.01); *C11B 5/0092* (2013.01); *C11B 9/00* (2013.01); *C12Y 110/03001* (2013.01); *C12Y 110/03002* (2013.01); *C12Y 114/18001* (2013.01)

(58) Field of Classification Search
None
See application file for complete search history.

(56) References Cited

U.S. PATENT DOCUMENTS

| | | | |
|---|---|---|---|
| 2004/0037792 A1* | 2/2004 | Hiramoto et al. | 424/65 |
| 2006/0062813 A1 | 3/2006 | Adachi et al. | |
| 2007/0178216 A1* | 8/2007 | Kandaswami et al. | 426/597 |

FOREIGN PATENT DOCUMENTS

| | | |
|---|---|---|
| JP | 9 227456 | 9/1997 |
| JP | 11 137224 | 5/1999 |
| JP | 11 169148 | 6/1999 |
| JP | 2001 346558 | 12/2001 |
| JP | 2002 244 | 1/2002 |
| JP | 2002 507887 | 3/2002 |
| JP | 2002 180081 | 6/2002 |
| JP | 2002 255778 | 9/2002 |
| JP | 2002 330741 | 11/2002 |
| JP | 2002 338990 | 11/2002 |
| JP | 2003-038144 A | 2/2003 |
| JP | 2003 79335 | 3/2003 |
| JP | 2003 82384 | 3/2003 |
| JP | 2003 96486 | 4/2003 |

(Continued)

OTHER PUBLICATIONS

Ueno et al, Inhibition of the formation of off-odor compounds from citral in an acidic aqueous solution, Flavour research at the dawn of the twenty-first century, proceedings of the weurman flavor research symposium, 10th, Beaune, France, 2002, 128-131.*

(Continued)

*Primary Examiner* — Qiuwen Mi
(74) *Attorney, Agent, or Firm* — Oblon, McClelland, Maier & Neustadt, L.L.P.

(57) ABSTRACT

The invention provides a deterioration inhibitor containing an amount of a product obtained by treatment of a tea extract with an oxidizing enzyme and then inactivating the enzyme. Addition of a deterioration inhibiting material according to the invention to a food or beverage or a cosmetic can inhibit deterioration of flavor and fragrance, with use in smaller amounts than conventional deterioration inhibitors. A particularly notable effect is exhibited against production of p-cresol and p-methylacetophenone which are citral-derived deterioration odor components, and therefore it is suitable for foods and beverages or cosmetics with citral-containing citrus-like flavors and fragrances.

19 Claims, 3 Drawing Sheets

(56) References Cited

FOREIGN PATENT DOCUMENTS

| JP | 2004-016059 A | 1/2004 |
| JP | 2004-016061 A | 1/2004 |
| JP | 2004 18613 | 1/2004 |
| JP | 2004-018756 A | 1/2004 |
| JP | 2005 171116 | 6/2005 |
| JP | 2006-036980 A | 2/2006 |
| JP | 2007-006758 A | 1/2007 |

OTHER PUBLICATIONS

Ho, Chi-Tang et al., "Oxidative Transformation of Tea Catechins", ACS Symp Ser (Am Chem Soc, No. 775, Chapter 7, pp. 102-112, (2001).

Schieberle, Peter et al., "Identification of Potent Flavor Compounds Formed in an Aqueous Lemon Oil/Citric Acid Emulsion", J. Agric. Food Chem., vol. 36, No. 4, pp. 797-800, (1988).

Office Action issued May 27, 2014 in Japanese Patent Application No. 2009-523618.

Y. Katsube, et al., "Production of useful eatechin derivatives by enzymatic processing of green tea extract", (Heisei 19) Japan Society for Bioscience, Biotechnology, and Agrochemistry Conference Abstracts, Mar. 5, 2007, p. 166, 3A06p06 (with English language translation).

\* cited by examiner

DEGRADATION INHIBITOR FOR FLAVOR OR AROMA

TECHNICAL FIELD

The present invention relates to a flavor or fragrance deterioration inhibitor and a flavor or fragrance deterioration inhibiting method which may be applied to a wide variety of materials that enter the human mouth during normal daily activities, such as beverages or foods, oral hygiene agents such as toothpastes and mouth odor inhibitors, or perorally administered drugs (these will collectively be referred to as "oral compositions"), flavoring agents, cosmetic products and the like.

BACKGROUND ART

Tastes and flavor of beverages and foods have a major influence on decrease or diminution of appetite, and therefore flavor is considered to be an element of dietary habit that is as important as nutrition. The fragrances imparted to cosmetics and toiletries such as soaps and shampoos are important elements for masking base odors and providing a pleasant sensation to the user or surrounding persons.

However, it is well known that the flavors and fragrance components in foods and beverages or in cosmetics are generally unstable and deteriorate by the effects of oxygen, light and heat, resulting in loss of the original flavors or fragrances, or generation of off-flavors or off-odors (deterioration odors), during various stages of production, distribution and storage.

Citral has a lemon-like fragrance and flavor, and is an important component used to impart a fresh, citrus sensation to products such as foods and beverages or cosmetics. Under acidic conditions, citral is known to undergo reactions such as cyclization, oxidation, hydration and isomerization, producing various off-flavor components [Peter Schieberle and Werner Grosch; J. Agric. Food Chem., Vol. 36, 797-800 (1988)].

Among the off-flavor components, p-methylacetophenone and p-cresol exhibit particularly strong deterioration odors and notably impair product quality.

Past efforts at inhibiting such deterioration of flavor and fragrance have included addition of various antioxidants or photodegradation inhibitors such as ascorbic acid (see Non-patent document 1).

Methods of adding plant extracts such as rosmarinic acid, perilla or peppermint to retard deterioration of citral have been disclosed (see Patent documents 1-11).

Methods of inhibiting deterioration of citral by addition of tea-derived components such as catechins and theaflavins have also been reported (see Patent documents 12-14).

However, deterioration of the flavors and fragrances of foods and beverages or cosmetics occurs not only as a result of the changes in the flavor and fragrance components themselves induced by oxygen, light and heat, but also due to a combination of numerous contributing reactions including oxidation, decomposition, isomerization and polymerization of different components such as fats and oils, proteins, saccharides, amino acids and organic acids in the foods and beverages or cosmetics. The inhibiting effect against deterioration has therefore often been inadequate with prior art methods, such that more powerful methods of retarding deterioration have been desired.

[Non-patent document 1] "Patent Office Report: Collection of Well-Known Prior Arts (Flavoring Agents), Section 1", Jan. 29, 1999 p 141-147

[Patent document 1] Japanese Patent Public Inspection No. 2002-507887
[Patent document 2] Japanese Unexamined Patent Publication HEI No. 11-137224
[Patent document 3] Japanese Unexamined Patent Publication HEI No. 11-169148
[Patent document 4] Japanese Unexamined Patent Publication No. 2001-346558
[Patent document 5] Japanese Unexamined Patent Publication No. 2002-244
[Patent document 6] Japanese Unexamined Patent Publication No. 2002-180081
[Patent document 7] Japanese Unexamined Patent Publication No. 2002-255778
[Patent document 8] Japanese Unexamined Patent Publication No. 2002-330741
[Patent document 9] Japanese Unexamined Patent Publication No. 2002-338990
[Patent document 10] Japanese Unexamined Patent Publication No. 2003-82384
[Patent document 11] Japanese Unexamined Patent Publication No. 2003-79335
[Patent document 12] Japanese Unexamined Patent Publication No. 2003-96486
[Patent document 13] Japanese Unexamined Patent Publication HEI No. 9-227456
[Patent document 14] Japanese Unexamined Patent Publication No. 2005-171116

DISCLOSURE OF THE INVENTION

Problems to be Solved by the Invention

The object of the present invention is to provide a deterioration inhibitor with an even stronger effect than the prior art against deterioration of flavors and fragrances in foods and beverages or cosmetics, which is attributed to a complex combination of factors.

Means for Solving the Problems

The present inventors investigated deterioration of citral by heat and methods of inhibiting it, and as a result we have discovered that products obtained by treating tea extract components with oxidizing enzymes exhibit notable effects of inhibiting production of p-cresol and p-methylacetophenone, which are citral-derived substances that cause very powerful deterioration odor.

Specifically, the present invention provides a flavor or fragrance deterioration inhibitor comprising as an effective component a product obtained by treatment of a tea extract component with an oxidizing enzyme. It further provides a flavor or fragrance deterioration inhibitor characterized in that the tea extract component is a dissolved component extracted from tea (*Camellia sinensis*) leaves, stems or buds using water, a polar organic solvent or a mixture thereof, in that the tea consists of tea leaves, stems or buds of unfermented tea, fermented tea, semi-fermented tea or post-fermented tea, in that the oxidizing enzyme is polyphenol oxidase, in that the flavor or fragrance is citrus, and in that the flavor or fragrance is based on citral.

The invention yet further provides flavoring agents, oral compositions and cosmetic products containing the flavor or fragrance deterioration inhibitor.

The invention still further provides a flavor or fragrance deterioration inhibiting method for a flavoring agent, oral composition or cosmetic product which involves addition of the aforementioned flavor or fragrance deterioration inhibitor.

Effect of The Invention

Addition of a deterioration inhibitor according to the invention to a flavoring agent or food or beverage can inhibit deterioration of flavor and fragrance caused by heat or light. A particularly notable effect is exhibited against deterioration of citral, inhibiting production of p-cresol and p-methylacetophenone which cause citral-derived deterioration odors, and maintaining a fresh citrus flavor and fragrance.

Moreover, because the polyphenol content is low compared to antioxidants, which are primarily polyphenols and are currently used as flavor and fragrance deterioration inhibitors for naturally derived food products, the effect on the taste of the final product is minimal and bitter and astringent tastes can be reduced. Sedimentation and coloration can also be reduced.

BEST MODE FOR CARRYING OUT THE INVENTION

Figure 1:
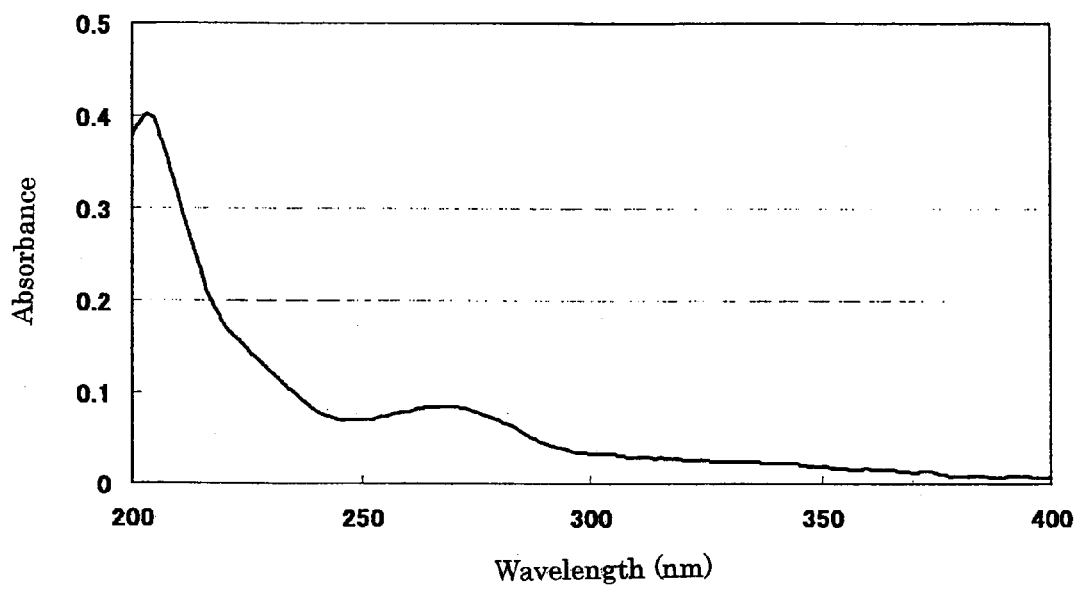
FIG. 1 is an ultraviolet absorption spectrum for the oxidizing enzyme-treated tea extract of Extract Example 1.

The present invention will now be explained in greater detail.
(1) Starting Materials The tea extract component used for the invention may be obtained by extraction from the leaves, stems or buds of tea (*Camellia sinensis*), an evergreen shrub of the Theaceae family, using water or a polar organic solvent.

Tea of any variety and locality may be used, and either raw tea leaves or pretreated tea leaves for beverage use (unfermented tea, semi-fermented tea, fermented tea or post-fermented tea) may be used.

The organic solvent used for extraction may contain water, and alcohol, acetone and ethyl acetate may be mentioned as polar organic solvents. Water or C2-4 aliphatic alcohols such as ethanol, propanol and butanol are preferred from the viewpoint of human safety and manageability, with water, ethanol and their mixtures (1-95% ethanol aqueous solutions) being especially preferred. The amount of solvent used for extraction may be selected as desired, but generally 2-200 parts by weight of solvent will be used for 1 part by weight of the starting material.
(2) Extraction Method The extraction method employed may be selected according to the type and amount of solvent. For example, the starting material may be placed in the solvent and extraction performed by an immersion or heated reflux method. An immersion method may be carried out under heated conditions, at room temperature or under cooled conditions.

In order to improve the extraction component yield and accomplish post-extraction separation and refining steps in a more efficient manner, a hydrolase such as pectinase, cellulase or tannase may be used in the solution either during or after extraction.

The residue that is insoluble in the solvent is then removed to obtain the extract, where the method of removing the residue may be any of various solid-liquid separation means such as centrifugal separation, filtration or pressing.
(3) Oxidizing Enzyme Treatment The oxidizing enzyme used for the invention may be polyphenol oxidase or peroxidase, with polyphenol oxidase being preferred.

Specifically there may be mentioned laccase (EC 1.10.3.2), catecholase (EC 1.10.3.1) and tyrosinase (EC1.14.18.1), which may be used alone or in combinations of two or more. There are no particular restrictions on the sources of the enzymes, and for example, there may be mentioned various enzymes derived from plants such as tea, or animal or bacterial enzymes.

Laccase is especially preferred among these because of its general utility and performance as an industrial enzyme, and because of its high oxidizing power. For example, the commercially available LACCASE DAIWA Y120 (trade name of Daiwa Fine Chemicals Co., Ltd.) and DENILITE II S (trade name of Novozymes, Japan) may be used. The enzyme does not necessarily need to be purified, and it may be used in the form of a crude enzyme.

The amount of enzyme used is 0.001-5 g and preferably 0.01-0.5 g with respect to 100 g of solid portion in the tea extract, where the amount of enzyme is calculated in terms of the effective amount of enzyme protein.

As an example, the reaction temperature for the enzyme treatment may be about 0-90° C. and preferably about 25-75° C., and the reaction time may be about 5 minutes-48 hours and preferably about 10 minutes-6 hours. The enzyme treatment is preferably followed by heating to reflux for at least 30 minutes in a ≥50% ethanol aqueous solution for deactivation of the enzyme.
(4) Purification Treatment The Oxidizing Enzyme Treatment Solution May be used after purifying treatment such as decoloring and deodorizing. The purifying treatment may employ active carbon, alumina, silica gel, a synthetic resin adsorbent comprising a porous styrene-divinylbenzene copolymer, or a methacrylic acid ester-based porous polymer resin or a gel-type synthetic adsorbent.

Examples of synthetic resin adsorbents for purification which may be used include DIAION HP-20 or DIAION SP-70 (trade names of Mitsubishi Chemical Corp.), AMBERLITE XAD-2 (trade name of Organo Corp.) and SEPHADEX LH-20 (trade name of Amersham Pharmacia Biotech). One or a combination of two or more selected from the group mentioned above may be used.
(5) Formulation The oxidizing enzyme treatment solution or its purified product may be added as a deterioration retarder directly to a food or beverage, or it may be prepared in the following manner prior to use.

For example, it may be dissolved to an appropriate concentration in a (mixed) solvent such as water, alcohol, glycerin, propylene glycol or the like (specifically a mixed solvent of water/ethanol, water/ethanol/glycerin or water/glycerin), to obtain a liquid agent. Alternatively, dextrin, sucrose, pectin, chitin or the like may be added, or they may be further concentrated to form a paste.

Also, an excipient (dextrin or the like) may be added to each solution and the mixture subjected to spray-drying to form a powder. The liquid agent may also be added to a fat or oil together with an emulsifier to form a dispersion, in order to obtain an oil-soluble liquid agent for preparation into various dosage forms depending on the purpose.

The deterioration inhibitor of the invention may be appropriately added during the production process for a flavoring agent, oral composition, cosmetic product or the like.

The amount of addition will differ depending on the product to which it is added, but an amount of 0.001-100 ppm as solid content is appropriate for a flavoring agent, oral composition or cosmetic product. If the product is an oral composition, the amount is preferably 0.01-30 ppm and especially 0.1-10 ppm from the viewpoint of almost completely avoiding effects on the original flavor.

In order to increase the flavor deterioration inhibiting effect, the deterioration inhibitor of the invention may be used in combination with a transition metal ion, with iron ion being particularly preferred from the viewpoint of human safety. There are no particular restrictions on the source for the iron ion, and metallic iron, iron salts or heme iron may be used. Specifically, there may be mentioned iron chloride, iron citrate, iron gluconate, iron lactate, iron pyrophosphate, iron sulfate and heme iron.

For increased deterioration inhibiting power, the deterioration inhibitor of the invention may be combined with commonly used antioxidants such as L-ascorbic acid, enzyme treated rutin, pagoda tree extract, grape seed extract, rosemary extract, green tea extract and the like, and in order to prevent coloration by reaction between metals and substrates there may be added a metal sequestering agent such as citric acid, gluconic acid, tartaric acid, phytic acid, pyrophosphoric acid or polyphosphoric acid.

A "flavor" according to the invention is the combination of both aroma, as the olfactory sensation of the oral composition in a food or beverage, and the taste perception of the portions exiting from the oral cavity into the nasal cavity. Flavor includes both the original flavor of an oral composition such as a food or beverage, and flavors imparted to the oral composition by addition of flavoring agents. "Fragrance" is the aroma perceived mainly by the olfactory sense, which is imparted by addition of flavoring agents to cosmetic products and the like.

The deterioration inhibitor of the invention is effective against deterioration of various kinds of flavors and fragrances, but it is most effective for deterioration of citrus-like flavors and fragrances.

It is particularly effective against deterioration of flavors and fragrances based on citral, with a notable effect of inhibiting production of p-methylacetophenone (cinnamon odor) and p-cresol (chemical odor) which cause very powerful citral-derived deterioration odor substances.

The deterioration inhibitor of the invention may be used for oral compositions, flavoring agents and cosmetic products without any particular restrictions, and the following may be mentioned as specific examples.

As examples of oral compositions there may be mentioned beverages, confectioneries, fats and oils or processed fat and oil food products, milk, dairy products, oral hygiene agents and the like, and more specifically, the following.

As examples of beverages there may be mentioned coffee, black tea, soft drinks, lactic acid bacteria beverages, non-juice beverages, juice-added beverages, vitamin drinks and the like, among which citrus-based carbonic acid beverages, juices, juice beverages, dairy beverages and tea beverages are particularly preferred.

As examples of confectioneries there may be mentioned jelly, pudding, bavarois, candies, biscuits, cookies, chocolate, cakes and the like, among which citral-containing cold desserts such as yogurt, jelly or ice cream and candies, rice jelly or gum and the like are particularly preferred.

As examples of fats and oils or processed fat and oil food products there may be mentioned edible fats and oils (animal fats and oils or vegetable fats and oils), margarine, shortening, mayonnaise, dressing, hard butter and the like, as well as instant (fried) noodles, fried tofu ("aburaage", "namaage" or "ganmodoki"), fried kamaboko, tempura, various fried foods and snacks (potato chips, fried "arare" crackers, fried dough cakes and doughnuts), processed frozen foods (frozen croquettes, fried shrimp, etc.), and the like.

As examples of milk or dairy products there may be mentioned milk such as raw milk, cow milk and processed milk, and dairy products such as cream, butter, butter oil, concentrated whey, cheese, ice cream, yogurt, condensed milk, powdered milk and concentrated milk.

As examples of oral hygiene agents there may be mentioned toothpastes, mouthwashes, mouth fresheners, mouth odor inhibitors and the like.

As examples of flavoring agents there may be mentioned flavoring materials (essential oils, essences, concretes, absolutes, extracts, oleoresins, resinoids, recovered flavors, carbon dioxide gas extracts, synthetic flavoring agents) and flavoring agent compositions containing them, among which citral-containing citrus-based flavoring agents are preferred.

As examples of cosmetic products there may be mentioned perfumes, cosmetics, cleansers, soaps, shampoos, rinses, bath additives, aromatic agents and the like, among which cosmetic products with citral-containing citrus-like aromas are particularly preferred. (See "Patent Office Report: Collection of Well-Known Prior Arts (Flavoring Agents)")

The present invention will now be explained in greater detail by the following examples, with the understanding that the invention is in no way intended to be restricted to the examples.

EXAMPLES

Extract Example 1

After adding 2000 g of water to 100 g of dried green tea leaves, the mixture was heated to reflux for 1 hour. The insoluble portion was removed by filtration, and then 0.04 g of laccase ("LACCASE DAIWA Y120, trade name of Daiwa Fine Chemicals Co., Ltd.) was added to the filtrate (solid content: 1.5-2.5%) prior to reaction at 55° C. for 4 hours.

After concentrating the enzyme treatment solution, 300 g of a 95% ethanol solution was added and the mixture was heated to reflux for 30 minutes for enzyme inactivation treatment.

The solution was cooled to −15° C., and then the insoluble portion was removed by filtration and the filtrate was concentrated under reduced pressure and freeze-dried to obtain 16.9 g of a dark brown powder (hereinafter referred to as "oxidizing enzyme-treated tea extract").

The physical properties of the extract were as follows.
a) The ultraviolet absorption spectrum is shown in FIG. 1 (measuring concentration: 10 ppm, diluting solvent: 70% ethanol solution).
λmax: 203 nm, 267 nm
b) Solubility: Soluble in water, readily soluble in 50-70% ethanol, insoluble in ethanol.

Extract Example 2

After adding 500 g of a 50% ethanol aqueous solution to 50 g of black tea leaves, the mixture was heated to reflux for 1 hour. After removing the insoluble portion by filtration, the filtrate was concentrated under reduced pressure and freeze-dried to obtain 15.1 g of a brown powder (hereinafter referred to as "black tea extract").

Figure 2:
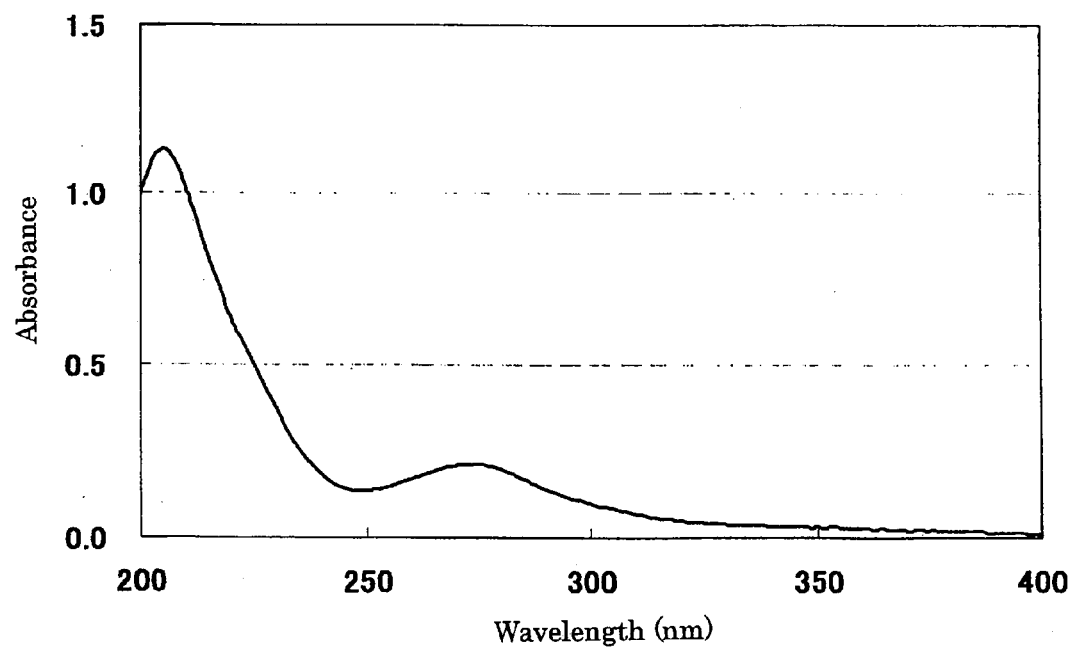
FIG. 2 is an ultraviolet absorption spectrum for the black tea extract of Extract Example 2.

The physical properties of the extract were as follows.
a) The ultraviolet absorption spectrum is shown in FIG. 2 (measuring concentration: 10 ppm, diluting solvent: 70% ethanol solution).
λmax: 205 nm, 273 nm
b) Solubility: Soluble in water, readily soluble in 50-70% ethanol, insoluble in ethanol.

In the test examples and examples, the following reagents and natural extracts were used as antioxidants currently employed as flavor and fragrance deterioration inhibitors.
1) L-ascorbic acid:
L(+)-ascorbic acid by Nacalai Tesque, Inc. was used.
2) Rutin:
α-G Rutin P (trade name) by Nacalai Tesque, Inc. was used.
3) Chlorogenic acid:
Chlorogenic acid by Wako Pure Chemical Industries, Ltd. was used.
4) Green tea extract:
Polyphenone KN (trade name) by Mitsui Norin Co., Ltd. was used.
5) Rosemary extract:
RM KEEPER SF (trade name) by Mitsubishi Chemical Corp. was used.
6) Grape seed extract:
GRAVINOL-F (trade name) by Kikkoman Corp. was used.

Test Example 1

The aforementioned "oxidizing enzyme-treated tea extract" was added to a lemon-flavored beverage, to examine its effect of inhibiting production of p-cresol and p-methylacetophenone.

A solution of 100 g of sugar, 1 g of citric acid, 1.5 g of a citral-containing lemon flavoring agent and 1 g of the present invention product in 100 g of a 50% ethanol aqueous solution was added in an amount of 1 g, and the total volume was adjusted to 1000 g with purified water.

Samples were prepared in the same manner by adding L-ascorbic acid, rutin, chlorogenic acid, rosemary extract, grape seed extract, green tea extract and the black tea extract of Extract Example 2, at concentrations of 2 ppm each. Each solution was sterilized at 70° C. for 10 minutes and then packed into a can to prepare a lemon-flavored beverage.

It was then stored in a thermostatic bath at 50° C. for 7 days. The amounts of p-cresol and p-methylacetophenone production in each lemon-flavored beverage were measured by high performance liquid chromatography.

Table 1 shows the amounts of p-cresol and p-methylacetophenone production for each sample, as relative values with respect to 100 as the amounts of p-cresol and p-methylacetophenone production after storage at 50° C. for 7 days without addition.

Test Example 2

The lemon-flavored beverage of Test Example 1 was subjected to an organoleptic evaluation with 10 trained panelists. As control lemon-flavored beverages there were used a refrigerated product without addition of the oxidizing enzyme-treated tea extract of the invention or antioxidants (evaluation points set to 1), and a product stored at 50° C. for 7 days without addition of the oxidizing enzyme-treated tea extract of the invention or antioxidants (evaluation points set to 5), and the degree of flavor deterioration of each lemon-flavored beverage was evaluated. The results are shown in Table 1.

The average points in the organoleptic evaluation shown in Table 1 are the average values by each panel, as rated on the following scale. The rating scale was the following for off-taste and off-odor (p-cresol (chemical odor) and p-methylacetophenone (cinnamon odor).
Very strongly notable: 5 points
Strongly notable: 4 points
Notable: 3 points
Weakly notable: 2 points
Not notable: 1 point

TABLE 1

Test results for Test Example 1 and Test Example 2

| Additives | Amount of p-cresol production | Amount of p-methylacetophenone production | Average points in organoleptic evaluation |
|---|---|---|---|
| Refrigerated product without addition | 0 | 0 | 1 |
| Product stored at 50° C. without addition | 100 | 100 | 5 |
| L-Ascorbic acid (2 ppm) | 112 | 100 | 4.3 |
| Rutin (2 ppm) | 100 | 102 | 4.4 |
| Chlorogenic acid (2 ppm) | 101 | 96 | 4.3 |
| Rosemary extract (2 ppm) | 87 | 88 | 3.5 |
| Grape seed extract (2 ppm) | 119 | 88 | 4.1 |
| Green tea extract (2 ppm) | 121 | 59 | 3.6 |
| Black tea extract (2 ppm) | 91 | 73 | 2.4 |
| Oxidizing enzyme-treated tea extract (2 ppm) | 59 | 55 | 2 |

Table 1 shows that addition of an oxidizing enzyme-treated tea extract of the invention to a lemon-flavored beverage significantly reduced production of p-cresol and p-methylacetophenone compared to products with addition of L-ascorbic acid, rutin, chlorogenic acid, rosemary extract, grape seed extract, green tea extract or black tea extract.

As clearly shown in Table 1, addition of an oxidizing enzyme-treated tea extract to lemon-flavored beverages inhibited p-cresol and p-methylacetophenone deterioration odors. The inhibiting effect was significantly greater than with L-ascorbic acid, rutin, chlorogenic acid, grape seed extract, green tea extract or black tea extract.

Test Example 3

Molecular Weight Distribution Measurement

The molecular weight distributions of the oxidizing enzyme-treated tea extract of Extract Example 1 and the black tea extract of Extract Example 2 were measured by size exclusion chromatography.

Figure 3:
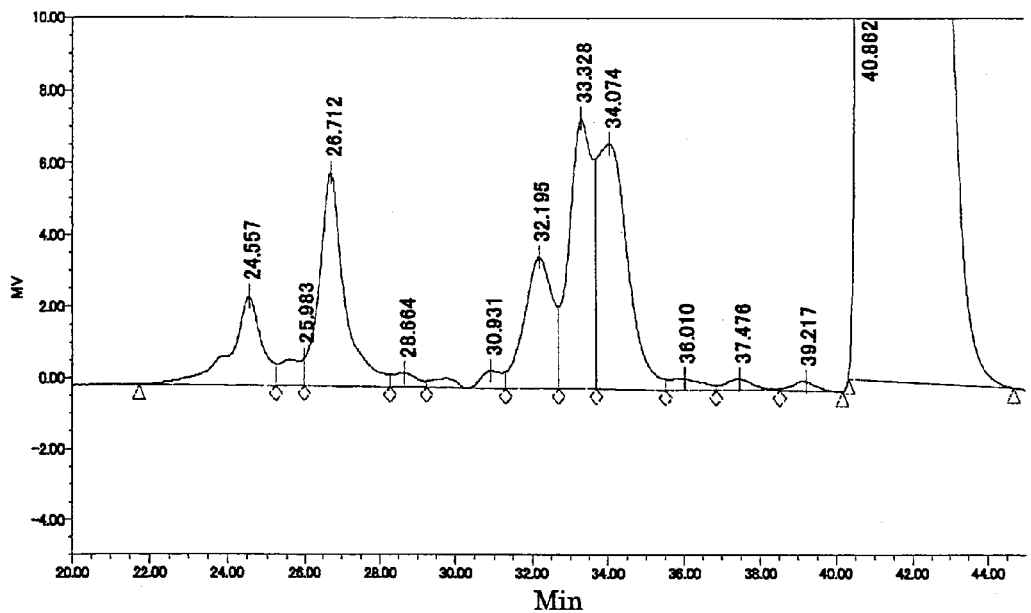
FIG. 3 is a size exclusion chromatogram for the oxidizing enzyme-treated tea extract of Extract Example 1. The horizontal axis represents retention time. The vertical axis represents molecular weight.
Figure 4:
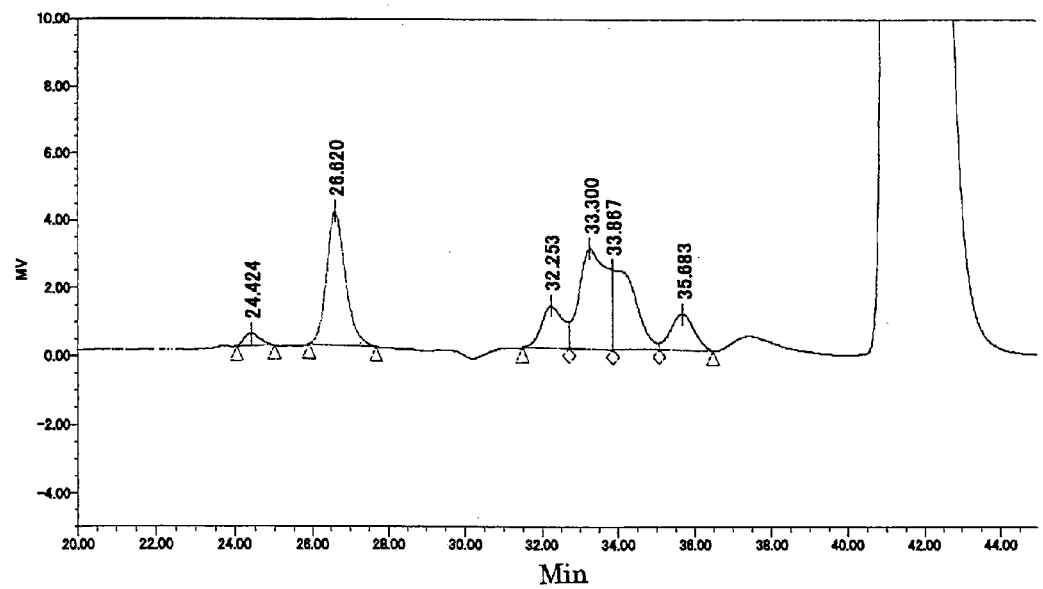
FIG. 4 is a size exclusion chromatogram for the black tea extract of Extract Example 2. The horizontal axis represents retention time. The vertical axis represents molecular weight.

The chromatograms for the oxidizing enzyme-treated tea extract and black tea extract are shown in FIG. 3 and FIG. 4, respectively. The measurement results for the molecular weight distribution are shown in Table 2.

The measuring device and measuring conditions were as follows.
Device: Waters 2690
Column: Asahipak GS-320+620+220 (7.6 mm i.d.×10 mm)+ (7.6 mm i.d.×500 mm)×2
Eluent: Distilled water+0.05% sodium azide
Flow rate: 1 mL/min
Detector: RI (Refractive Index) detector, PDA (Photo Diode Array) detector
Injection volume: 100 µL
Column temperature: 40° C.

Figure 5:
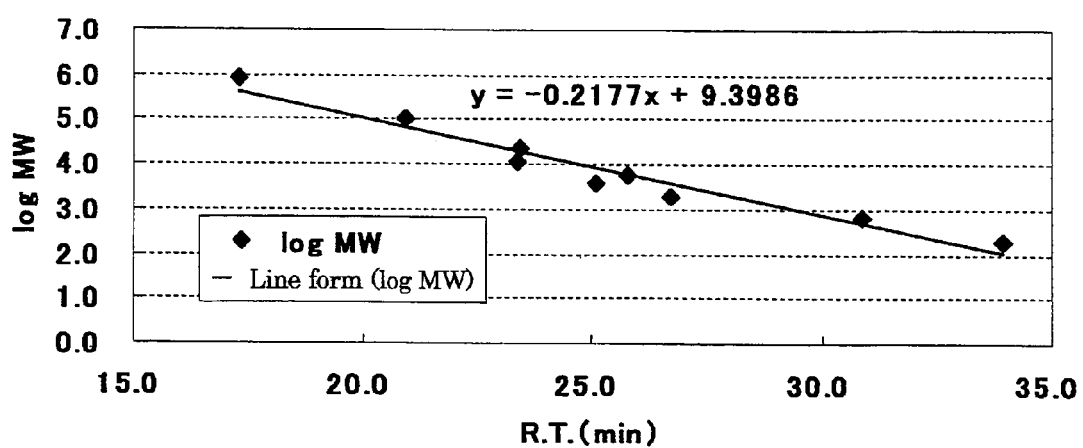
FIG. 5 is a graph showing the calibration curve data for a standard solution. The horizontal axis represents retention time. The vertical axis represents logarithm of molecular weight.

The molecular weight distribution was determined from a calibration curve (FIG. 5) prepared using the following standard solutions.
Standard solution 1: Pullulan aqueous solution (pullulan MW 800,000, 100,000, 20,000, 6000; each in 0.01% mixed solution with glucose) (product of Polymer Laboratories).
Standard solution 2: Polyethylene glycol aqueous solution (PEG MW 10,000, 4000, 2000, 600; each in 0.01% mixed solution with glucose) (product of Shodex)

TABLE 2

Molecular weight distribution measurement results

| Molecular weight (MW) | Oxidizing enzyme-treated tea extract (area %) | Black tea extract (area %) |
|---|---|---|
| <3000 | 67.9 | 70.3 |
| 3000-10,000 | 22.6 | 27.7 |
| 10,000-15,000 | 7 | 2 |
| >15,000 | 2.5 | 0 |

Table 2 shows that the oxidizing enzyme-treated tea extracts contained significantly more components with molecular weights of 10,000 and greater, compared to the black tea extract.

Test Example 4

Measurement of Total Polyphenol Content

The total polyphenol contents of the oxidizing enzyme-treated tea extracts of the invention and existing antioxidant substances were measured in the following manner according to the Folin-Denis method.

This method performs colorimetry, measuring the blue color produced by reduction of molybdic acid in alkali solution by the phenolic hydroxyl groups of tannin-like compounds.

A 100 µl portion of each sample adjusted to 50 ppm, 25 ppm, 12.5 ppm and 6.25 ppm with purified water was prepared, and 100 µl of Folin-Denis reagent was added to each and stirred therewith for 2 minutes, after which the mixture was allowed to stand at room temperature for 3 minutes. Next, 100 µl of a 10% (W/V) sodium hydrogencarbonate solution was added to each, and the mixture was stirred for 2 minutes and then reacted for 1 hour in a dark area. The absorbance at 655 nm was measured with a microplate reader, and the polyphenol concentration of each sample was calculated based on a calibration curve for tannic acid.

Preparation of Folin-Denis reagent: After combining 100 g of sodium tungstate, 20 g of phosphomolybdic acid, 50 ml of phosphoric acid and 750 ml of water, the mixture was heated to reflux for 2 hours and then allowed to cool, after which water was added to a total volume of 1000 ml.

The results are shown in Table 3.

TABLE 3

Total polyphenol content measurement results

| Sample | Polyphenol content (%) |
|---|---|
| Rutin | 43.3 |
| Rosemary extract | 33.4 |
| Grape seed extract | 77.4 |
| Green tea extract | 42 |
| Black tea extract | 46.1 |
| Oxidizing enzyme-treated tea extract | 19.9 |

In Table 1 it was shown that the oxidizing enzyme-treated tea extracts clearly exhibit the highest effects of inhibiting deterioration of lemon-flavored beverages, but Table 3 shows that the polyphenol contents of the oxidizing enzyme-treated tea extracts were lower than those of existing antioxidants. In other words, this result suggests that the oxidizing enzyme-treated tea extracts of the invention exhibit flavor and fragrance deterioration inhibiting effects by a different mechanism than the antioxidant effect based mainly on polyphenols which is exhibited by existing flavor deterioration inhibitors.

Test Example 5

100% Orange Beverage

A 160 g portion of distilled water was added to and mixed with 40 g of 5-fold Valencia Orange concentrate. The oxidizing enzyme-treated tea extract of Extract Example 1 was then added at 2 ppm, and after filling the mixture into a glass container, it was sterilized (70° C., 10 minutes) to prepare a 100% orange beverage. The obtained 100% orange beverage was evaluated by a trained panel, which evaluated it as being free of off-taste and off-odor and having a satisfactory flavor.

Samples were prepared in the same manner by adding L-ascorbic acid, rutin, chlorogenic acid, rosemary extract, grape seed extract, green tea extract and the black tea extract of Extract Example 2, at concentrations of 2 ppm each.

The samples were stored in a thermostatic bath at 50° C. for 7 days for heat abuse.

Following the heat abuse, an organoleptic evaluation was conducted with 10 trained panelists. As control 100% orange beverages there were used a refrigerated product without addition of the oxidizing enzyme-treated tea extract of the invention or antioxidants (evaluation points set to 1), and a product stored at 50° C. for 7 days without addition of the oxidizing enzyme-treated tea extract of the invention or antioxidants (evaluation points set to 5), and the degree of flavor deterioration of each 100% orange beverage was evaluated. The results are shown in Table 4.

The average points in the organoleptic evaluation shown in Table 4 are the average values by each panel, as rated on the following scale.

The rating scale was the following for off-taste and off-odor (potato odor, spice odor).
Very strongly notable: 5 points
Strongly notable: 4 points
Notable: 3 points
Weakly notable: 2 points
Not notable: 1 point

TABLE 4

Organoleptic evaluation results for heating test
with 100% orange beverage

| Additives | Average points in organoleptic evaluation |
|---|---|
| Refrigerated product without addition | 1.0 |
| Product stored at 50° C. without addition | 5.0 |
| L-Ascorbic acid (2 ppm) | 4.4 |
| Rutin (2 ppm) | 4.0 |
| Chlorogenic acid (2 ppm) | 4.0 |
| Rosemary extract (2 ppm) | 3.4 |
| Grape seed extract (2 ppm) | 4.4 |
| Green tea extract (2 ppm) | 3.7 |
| Black tea extract (2 ppm) | 2.7 |
| Oxidizing enzyme-treated tea extract (2 ppm) | 2.0 |

As clearly shown in Table 4, addition of an oxidizing enzyme-treated tea extract to a 100% orange beverage inhibited the deterioration odors of potato odor and spice odor. The inhibiting effect was significantly greater than with L-ascorbic acid, rutin, chlorogenic acid, rosemary extract, grape seed extract, green tea extract or black tea extract.

Test Example 6

Sterilized Lactic Acid Bacteria Beverage

Distilled water was added to 20 g of a fermented milk stock solution (total solid content: 54%, defatted milk solid content: 4%) for dilution to a total of 100 g. There were then added 0.1 g of a lemon flavoring agent and the oxidizing enzyme-treated tea extract of Extract Example 1 to 2 ppm, and after filling the mixture into a glass container, it was sterilized (70° C., 10 minutes) to prepare a sterilized lactic acid bacteria beverage. The obtained sterilized lactic acid bacteria beverage was evaluated by a trained panel, which evaluated it as being free of off-taste and off-odor and having a satisfactory flavor.

Samples were prepared in the same manner by adding L-ascorbic acid, rutin, chlorogenic acid, rosemary extract, grape seed extract, green tea extract and the black tea extract of Extract Example 2, at concentrations of 2 ppm each.

The samples were irradiated with light (fluorescent lamp) in a light stability tester at 15,000 lux, 5° C., 12 hours for light abuse, and then an organoleptic evaluation was conducted with 10 trained panelists. As control samples there were used a product without irradiation by the fluorescent lamp and without addition of the oxidizing enzyme-treated tea extract of the invention or antioxidants (evaluation points set to 1), and a product irradiated with the fluorescent lamp at 15,000 lux, 5° C., 7 days, without addition of the oxidizing enzyme-treated tea extract of the invention or antioxidants (evaluation points set to 5), and the degree of flavor deterioration of each sterilized lactic acid bacteria beverage was evaluated. The results are shown in Table 5.

The average points in the organoleptic evaluation shown in Table 5 are the average values by each panel, as rated on the following scale.

The rating scale was the following for off-taste and off-odor (pickle odor, metallic odor).

Very strongly notable: 5 points
Strongly notable: 4 points
Notable: 3 points
Weakly notable: 2 points
Not notable: 1 point

TABLE 5

Organoleptic evaluation results for light abuse
test with sterilized lactic acid bacteria beverage

| Additives | Average points in organoleptic evaluation |
|---|---|
| Product without fluorescent lamp irradiation | 1.0 |
| Fluorescent lamp-irradiated product without addition | 5.0 |
| L-Ascorbic acid (2 ppm) | 4.3 |
| Rutin (2 ppm) | 4.1 |
| Chlorogenic acid (2 ppm) | 4.1 |
| Rosemary extract (2 ppm) | 3.2 |
| Grape seed extract (2 ppm) | 4.2 |
| Green tea extract (2 ppm) | 3.5 |
| Black tea extract (2 ppm) | 2.2 |
| Oxidizing enzyme-treated tea extract (2 ppm) | 1.9 |

As clearly shown in Table 5, addition of an oxidizing enzyme-treated tea extract to the sterilized lactic acid bacteria beverage inhibited the deterioration odors of pickle odor and metallic odor. The inhibiting effect was significantly greater than with L-ascorbic acid, rutin, chlorogenic acid, rosemary extract, grape seed extract, green tea extract or black tea extract.

Test Example 7

Gum

After adding 0.5 g of a herb flavoring agent and 5 ppm of the oxidizing enzyme-treated tea extract of Extract Example 1 to 50 g of gum base, a kneader was used for kneading and the mixture was molded. The flavor of the obtained gum was evaluated by a trained panel, which evaluated it as being satisfactorily free of off-taste and off-odor.

Samples were prepared in the same manner by adding L-ascorbic acid, rutin, chlorogenic acid, rosemary extract, grape seed extract, green tea extract and the black tea extract of Extract Example 2, at concentrations of 5 ppm each.

The samples were irradiated with light (fluorescent lamp) in a light stability tester at 15,000 lux, 5° C., 7 days for light abuse, and then an organoleptic evaluation was conducted with 10 trained panelists. As control samples there were used a product without irradiation by the fluorescent lamp and without addition of the oxidizing enzyme-treated tea extract of the invention or antioxidants (evaluation points set to 1), and a product irradiated with the fluorescent lamp at 5° C., 15,000 lux, 7 days, without addition of the oxidizing enzyme-treated tea extract of the invention or antioxidants (evaluation points set to 5), and the degree of flavor deterioration of each sample was evaluated. The results are shown in Table 6.

The average points in the organoleptic evaluation shown in Table 6 are the average values by each panel, as rated on the following scale.

The rating scale was the following for off-taste and off-odor (egg flavor, gum odor).

Very strongly notable: 5 points
Strongly notable: 4 points
Notable: 3 points
Weakly notable: 2 points
Not notable: 1 point

TABLE 6

Organoleptic evaluation results for light abuse test with gum

| Additives | Average points in organoleptic evaluation |
|---|---|
| Product without fluorescent lamp irradiation | 1.0 |
| Fluorescent lamp-irradiated product without addition | 5.0 |
| L-Ascorbic acid (5 ppm) | 4.5 |
| Rutin (5 ppm) | 4.2 |
| Chlorogenic acid (5 ppm) | 4.2 |
| Rosemary extract (5 ppm) | 3.7 |
| Grape seed extract (5 ppm) | 4.4 |
| Green tea extract (5 ppm) | 4.0 |
| Black tea extract (5 ppm) | 3.6 |
| Oxidizing enzyme-treated tea extract (2 ppm) | 3.3 |

As clearly shown in Table 6, addition of an oxidizing enzyme-treated tea extract to the gum inhibited the deterioration odors of harsh taste and rubber like odor. The inhibiting effect was significantly greater than with L-ascorbic acid, rutin, chlorogenic acid, rosemary extract, grape seed extract, green tea extract or black tea extract.

Test Example 8

Japanese Dressing

After combining 150 g of vinegar, 50 g of high-fructose corn syrup, 30 g of table salt, 2 g of sodium glutamate, 1 g of spice, 2 g of a thickener, 2 g of an emulsifier, 400 g of corn oil, 362 g of water and 1 g of yuzu (Citrus junos) flavoring, the mixture was uniformly stirred. The oxidizing enzyme-treated tea extract of Extract Example 1 was then added at 2 ppm, and after filling the mixture into a glass container, it was sterilized (70° C., 10 minutes) to prepare a Japanese dressing. The flavor of the obtained Japanese dressing was evaluated by a trained panel, which evaluated it as being satisfactory without loss of original flavor.

Samples were prepared in the same manner by adding L-ascorbic acid, rutin, chlorogenic acid, rosemary extract, grape seed extract, green tea extract and the black tea extract of Extract Example 2, at concentrations of 2 ppm each.

The samples were stored in a thermostatic bath at 30° C. for 10 days for heat abuse.

An organoleptic evaluation was conducted with 10 trained panelists. As control samples there were used a refrigerated product without addition of the oxidizing enzyme-treated tea extract of the invention or antioxidants (evaluation points set to 1), and a product stored at 30° C. for 10 days without addition of the oxidizing enzyme-treated tea extract of the invention or antioxidants (evaluation points set to 5), and the degree of flavor deterioration of each Japanese dressing was evaluated. The results are shown in Table 7.

The average points in the organoleptic evaluation shown in Table 7 are the average values by each panel, as rated on the following scale.

The rating scale was the following for off-taste and off-odor (fat deterioration (aldehyde) odor, metallic odor).

Very strongly notable: 5 points
Strongly notable: 4 points
Notable: 3 points
Weakly notable: 2 points
Not notable: 1 point

TABLE 7

Organoleptic evaluation results for heating test with dressing

| Additives | Average points in organoleptic evaluation |
|---|---|
| Refrigerated product without addition | 1.0 |
| Product stored at 30° C. without addition | 5.0 |
| L-Ascorbic acid (2 ppm) | 4.3 |
| Rutin (2 ppm) | 4.0 |
| Chlorogenic acid (2 ppm) | 3.9 |
| Rosemary extract (2 ppm) | 3.1 |
| Grape seed extract (2 ppm) | 4.0 |
| Green tea extract (2 ppm) | 4.1 |
| Black tea extract (2 ppm) | 3.2 |
| Oxidizing enzyme-treated tea extract (2 ppm) | 2.7 |

As clearly shown in Table 7, addition of an oxidizing enzyme-treated tea extract to the dressing inhibited the deterioration odors of aldehyde-like fat deterioration odor and metallic odor. The inhibiting effect was significantly greater than with L-ascorbic acid, rutin, chlorogenic acid, rosemary extract, grape seed extract, green tea extract or black tea extract.

Test Example 9

Cosmetic Water

The following components were combined to prepare cosmetic water by an ordinary method.

| | |
|---|---|
| 1,3-Butylene glycol | 60.0 g |
| Glycerin | 40.0 g |
| Oleyl alcohol | 1.0 g |
| POE (20) Sorbitan monolauric acid ester | 5.0 g |
| POE (15) Lauryl alcohol ether | 5.0 g |
| 95% Ethanol | 100.0 g |
| Aromatic | 2.0 g |
| Methylparaben | 1.0 g |
| Gardenia yellow pigment | 0.1 g |
| 1 wt %/70 wt % Aqueous ethanol solution of oxidizing enzyme-treated tea extract | 2.0 g |
| Purified water | 783.9 g |

The obtained cosmetic water was evaluated by a trained panel, which evaluated it as having no off-odor and retaining the original aroma of cosmetic water.

Samples were prepared in the same manner by adding L-ascorbic acid, rutin, chlorogenic acid, rosemary extract, grape seed extract, green tea extract and the black tea extract of Extract Example 2, at concentrations of 2 ppm each, instead of the oxidizing enzyme-treated tea extract of the invention in the formulation described above.

The samples were stored in a thermostatic bath at 50° C. for 7 days for heat abuse.

An organoleptic evaluation was conducted with 10 trained panelists. As control samples there were used a refrigerated product without addition of the oxidizing enzyme-treated tea extract of the invention or antioxidants (evaluation points set to 1), and a product stored at 50° C. for 7 days without addition of the oxidizing enzyme-treated tea extract of the invention or antioxidants (evaluation points set to 5), and the degree of aroma deterioration of each cosmetic water was evaluated. The results are shown in Table 8.

The average points in the organoleptic evaluation shown in Table 8 are the average values by each panel, as rated on the following scale.

The rating scale was the following for off-odor (chemical odor, metallic odor).
Very strongly notable: 5 points
Strongly notable: 4 points
Notable: 3 points
Weakly notable: 2 points
Not notable: 1 point

TABLE 8

Organoleptic evaluation results for heating test with cosmetic water

| Additives | Average points in organoleptic evaluation |
|---|---|
| Refrigerated product without addition | 1.0 |
| Product stored at 50° C. without addition | 5.0 |
| L-Ascorbic acid (2 ppm) | 4.0 |
| Rutin (2 ppm) | 4.1 |
| Chlorogenic acid (2 ppm) | 4.4 |
| Rosemary extract (2 ppm) | 3.4 |
| Grape seed extract (2 ppm) | 4.3 |
| Green tea extract (2 ppm) | 3.6 |
| Black tea extract (2 ppm) | 2.8 |
| Oxidizing enzyme-treated tea extract (2 ppm) | 2.1 |

As clearly shown in Table 8, addition of an oxidizing enzyme-treated tea extract to the cosmetic water inhibited the deterioration odors of chemical odor and metallic odor. The inhibiting effect was significantly greater than with L-ascorbic acid, rutin, chlorogenic acid, rosemary extract, grape seed extract, green tea extract or black tea extract.

Example 1

Vanilla Extract

To 10 g of vanilla beans there were added 35 g of ethanol and 65 g of distilled water, and the mixture was allowed to stand at room temperature in a dark area for 4 weeks for extraction. The solution was filtered to obtain 90 g of vanilla extract. To 90 g of the extract there was then added 10 g of a 1 wt %/70 wt % aqueous ethanol solution of an oxidizing enzyme-treated tea extract to obtain a vanilla extract according to the invention. The obtained vanilla extract was evaluated by a trained panel, which evaluated it as having no off-taste or off-odor and retaining the original flavor of vanilla.

Example 2

Candy

After combining 141 g of rice jelly, 180 g of granulated sugar and 60 g of water, the mixture was heated to 155° C. After then cooling to 120° C., 6 g of citric acid, 0.6 g of a citrus flavoring agent and 0.1 g of a 1 wt %/70 wt % aqueous ethanol solution of an oxidizing enzyme-treated tea extract were added, and the mixture was shaped and cooled. The obtained candy was evaluated by a trained panel, which evaluated it as being free of off-taste and off-odor and retaining a satisfactory flavor.

Example 3

Margarine

After combining 55 g of shortening, 15 g of corn oil, 0.1 g of a 30%-carotene solution, 0.2 g of lecithin and 0.3 g of an emulsifier, the mixture was sterilized at 80° C., 10 minutes with a hot water bath. Separately, 27.9 g of water, 0.5 g of table salt, 1 g of skim milk powder and 0.1 g of a 1 wt %/70 wt % aqueous ethanol solution of the oxidizing enzyme-treated tea extract were mixed and heated to 85° C. in a hot water bath. The corn oil mixture and skim milk powder mixture obtained in this manner were cooled to 50-60° C. and then combined, and a Disper mixer was used for stirring at 1,500 rpm for 5 minutes while cooling with ice water. After thoroughly kneading the entire mixture with a rubber spatula while cooling with water (to 10° C.), it was transferred to a container and aged overnight in a refrigerator to obtain margarine. The obtained margarine was evaluated by a trained panel, which evaluated it as being free of off-taste and off-odor and retaining the original flavor of margarine.

Example 4

Oral Cleaning Agent

The following components were combined to prepare an oral cleaning agent by an ordinary method.

| Ethanol | 15.00 g |
|---|---|
| Glycerin | 10.00 g |
| Polyoxyethylene hydrogenated castor oil | 2.00 g |
| Saccharin sodium | 0.15 g |
| Sodium benzoate | 0.05 g |
| flavor | 0.30 g |
| Disodium hydrogenphosphate | 0.10 g |
| Coloring agent | 0.20 g |
| 1 wt %/70 wt % Aqueous ethanol solution of oxidizing enzyme-treated tea extract | 0.10 g |
| Purified water | 72.10 g |

Example 5

Apple Flavor

The following components were combined to prepare an apple flavor by an ordinary method.

| Isoamyl formate | 100 g |
|---|---|
| Isoamyl acetate | 100 g |
| Isoamyl hexanoate | 60 g |
| Isoamyl octanoate | 10 g |
| Geraniol | 10 g |
| Ethanol | 430 g |
| Purified water | 290 g |

To 100 g of the apple flavor there was then added 2.0 g of a 1 wt %/70 wt % aqueous ethanol solution of an oxidizing enzyme-treated tea extract to obtain an apple flavor according to the invention. The obtained apple flavor was evaluated by a trained panel, which evaluated it as being free of off-taste and off-odor and retaining the original flavor of apple.

Example 6

Grape Flavor

The following components were combined to prepare a grape flavor by an ordinary method.

| Isoamyl isovalerate | 10 g |
|---|---|
| Cinnamyl alcohol | 5 g |
| Ethyl acetate | 60 g |
| Ethyl butyrate | 15 g |
| Ethyl 3-methyl-3-phenylglycidate | 10 g |

-continued

| | |
|---|---|
| Ethyl heptanoate | 8 g |
| Methyl anthranilate | 130 g |
| Methyl salicylate | 15 g |
| Ethanol | 373 g |
| Purified water | 374 g |

To 100 g of the grape flavor there was then added 1.0 g of a 1 wt %/70 wt % aqueous ethanol solution of an oxidizing enzyme-treated tea extract to obtain a grape flavor according to the invention. The obtained grape flavor was evaluated by a trained panel, which evaluated it as being free of off-taste and off-odor and retaining the original flavor of grape.

INDUSTRIAL APPLICABILITY

The oxidizing enzyme-treated tea extract of the invention can retard deterioration of flavor and fragrance caused by heat or light even when added in small amounts and has a particularly notable effect of inhibiting citral deterioration, and it can therefore be used in a wide range of products including foods, beverages, cosmetics.

The invention claimed is:

1. A flavor or fragrance deterioration inhibitor comprising as an effective amount of a product prepared by a process comprising
    extracting a tea extract component from tea leaves, stems or buds with a solvent, wherein the tea is *Camellia sinensis*,
    treating the tea extract component with an oxidizing enzyme to yield an oxidized component, and
    inactivating the oxidizing enzyme by heating thereby yielding a flavor or fragrance deterioration inhibitor.

2. The flavor or fragrance deterioration inhibitor according to claim 1, wherein the the solvent is water, a polar organic solvent or a mixture thereof.

3. The flavor or fragrance deterioration inhibitor according to claim 1, wherein the tea consists of tea leaves, stems or buds of unfermented tea, fermented tea, semi-fermented tea or post-fermented tea.

4. The flavor or fragrance deterioration inhibitor according to claim 1, wherein the oxidizing enzyme is polyphenol oxidase.

5. The flavor or fragrance deterioration inhibitor according to claim 1, wherein the flavor or fragrance is citrus.

6. The flavor or fragrance deterioration inhibitor according to claim 1, wherein the flavor or fragrance is based on citral.

7. A flavoring or fragrance containing a flavor or fragrance deterioration inhibitor according to claim 1.

8. An oral composition comprising a flavoring according to claim 7.

9. A cosmetic product comprising a fragrance according to claim 7.

10. An oral composition comprising a flavor or fragrance deterioration inhibitor according to claim 1.

11. A cosmetic product comprising a flavor or fragrance deterioration inhibitor according to claim 1.

12. The flavor or fragrance deterioration inhibitor according to claim 1, wherein said inactivation treatment of the oxidizing enzyme is the treatment of heating to reflux for at least 30 minutes in a 50% or more ethanol aqueous solution.

13. The flavor or fragrance deterioration inhibitor according to claim 1, wherein the process further comprises after the inactivating, purifying the oxidized tea extract component.

14. The flavor or fragrance deterioration inhibitor according to claim 13, wherein the purifying comprises contacting the oxidized tea extract component with an active carbon, an alumina, a silica gel, a synthetic resin adsorbent comprising a porous styrene-divinylbenzene copolymer, a methacrylic acid ester-based porous polymer resin, or a gel-type synthetic adsorbent.

15. A flavor or fragrance deterioration inhibiting method for a flavoring, fragrance, oral composition or cosmetic product, comprising adding a flavor or fragrance deterioration inhibitor according to claim 1 to the flavoring, fragrance, oral composition or cosmetic product.

16. The flavor or fragrance deterioration inhibiting method according to claim 15, wherein the flavor or fragrance is citrus-series.

17. The flavor or fragrance deterioration inhibiting method according to claim 15, wherein the flavor or fragrance is based on citral.

18. The flavor or fragrance deterioration inhibiting method according to claim 17, wherein the generation of deterioration odors caused by heat or light is inhibited.

19. The flavor or fragrance deterioration inhibiting method according to claim 18, wherein the deterioration odor is a deterioration odor due to p-cresol or p-methylacetophenone.

* * * * *